United States Patent [19]

Cuccia

[11] Patent Number: 4,915,101

[45] Date of Patent: Apr. 10, 1990

[54] ROTATABLE TREATMENT TABLE HAVING ADJUSTABLE SUPPORT ASSEMBLIES

[76] Inventor: David F. Cuccia, 227 Jackson Ave., Syosset, N.Y. 11791

[21] Appl. No.: 125,973

[22] Filed: Nov. 27, 1987

Related U.S. Application Data

[63] Continuation-in-part of Ser. No. 3,811, Jan. 16, 1987, abandoned.

[51] Int. Cl.[4] .............................................. A61F 5/00
[52] U.S. Cl. ........................................ 128/73; 128/74
[58] Field of Search ...................... 178/70, 71, 72, 73, 178/74

[56] References Cited

U.S. PATENT DOCUMENTS

| | | | |
|---|---|---|---|
| 1,079,795 | 11/1913 | Naysmith | 128/73 |
| 1,117,403 | 11/1914 | Kreitzer | 128/72 |
| 1,386,901 | 8/1921 | Schreiner | 128/73 |
| 1,529,872 | 3/1925 | Craig | 128/71 |
| 1,591,551 | 7/1926 | Daniel | 128/73 |
| 1,735,703 | 11/1929 | Williams | 128/73 |
| 2,283,549 | 6/1942 | Galbraith | 128/71 |
| 2,630,800 | 3/1953 | Voss et al. | 128/73 |
| 2,915,057 | 12/1959 | Ammon | 128/71 |
| 3,081,085 | 3/1963 | Girolamo | 128/71 |
| 3,207,152 | 9/1965 | Thornton | 128/70 |
| 4,271,830 | 6/1981 | Moon | 128/73 |
| 4,401,110 | 8/1983 | Ekholm | 128/73 |
| 4,546,764 | 10/1985 | Gerber | 128/55 |
| 4,672,697 | 6/1987 | Schürch | 128/74 |
| 4,739,749 | 4/1988 | Lindley | 128/71 |

FOREIGN PATENT DOCUMENTS

| | | | |
|---|---|---|---|
| 2584922 | 1/1987 | France | 128/74 |

*Primary Examiner*—Edgar S. Burr
*Assistant Examiner*—Tonya Lamb
*Attorney, Agent, or Firm*—M. K. Silverman

[57] ABSTRACT

A rotatable treatment table for effecting extensions and flexions of the spine. The treatment table includes a weighted platform adapted to rest upon a floor. Rigid support elements having upper and lower ends are provided. Further provided is an extensible elevation member having a lower and an upper end, the lower end secured to the platform, in which the rotational movement of the upper end of the extensible elevation member relative to the lower end occurs. Yet further provided is a rectangular supportive frame proportioned to extend beyond the length of the body of a patient. The rigid support is pivotally secured near its center of gravity to the upper end of the rigid elevation member. Further, it is pivotally secured to the upper end of the extensible elevation member. The pivotal securements permit the support frame to define a selectable curved path relative to the platform. Also included in the treatment table is a center and lower back support assembly transversely mounted to the rigid frame near to the upper ends of the extensible elevation members, the center of gravity of the patient being located substantially within the extent of the assembly within the rigid frame.

23 Claims, 7 Drawing Sheets

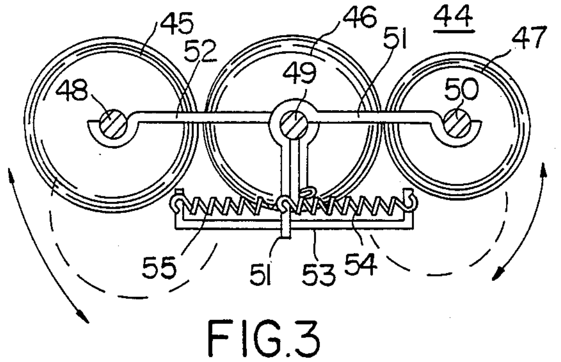
FIG.3
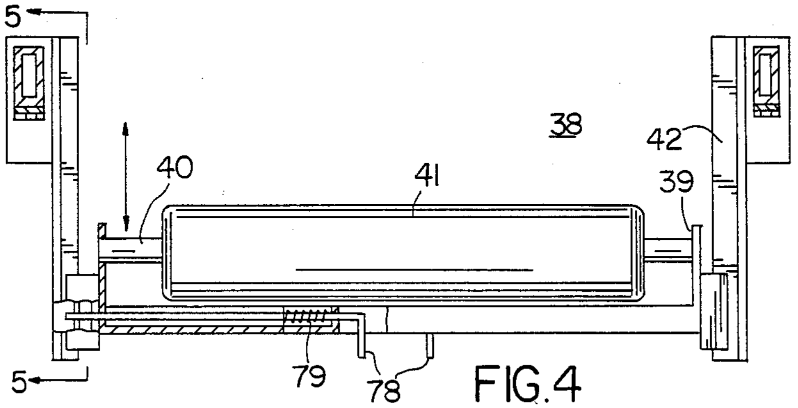
FIG.4
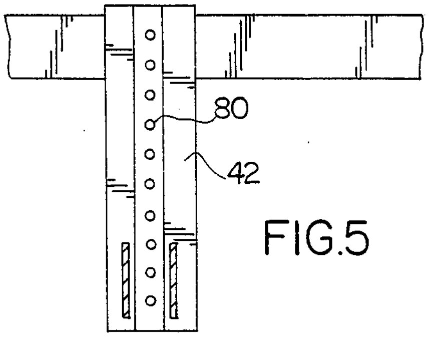
FIG.5
44 FIG.6
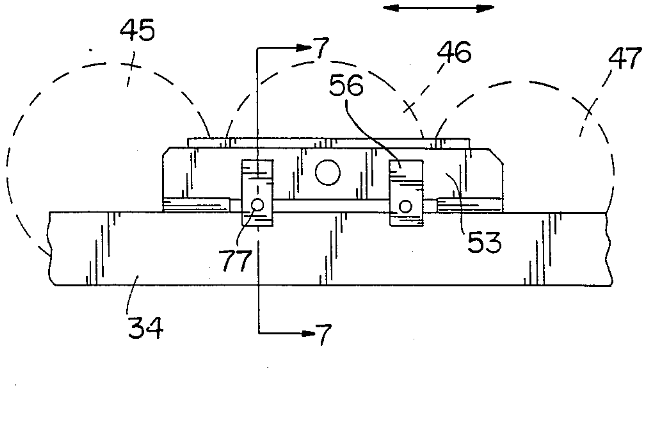
FIG.7
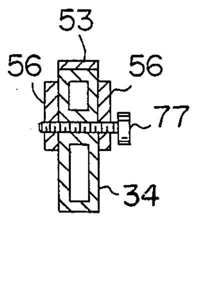

ROTATABLE TREATMENT TABLE HAVING ADJUSTABLE SUPPORT ASSEMBLIES

REFERENCE TO RELATED APPLICATION

This is a continuation in part of application Ser. No. 07/003,811, filed Jan. 16, 1987, now abandoned.

BACKGROUND OF THE INVENTION

Numerous devices, including chiropractic, osteopatic, obstetrical, delivery, x-ray, operating and embalming tables, which suspend or position a patient in a particular way for some special purpose, are known in the art.

U.S. Pat. No. 4, 292,962 (1981) to Krause presents an apparatus for effecting postural treatment of humans in which the patent, while resting face down on a pivoting platform, can vary the position of his arms, adjust his center of gravity while in suspension and, thereby, affect his posture upon the table.

U.S. Pat. No. 3, 568, 669 (1971) to Stites discloses a posture board wherein the patient is rotated 180 degrees from an initial upright position on his back to one of complete inversion, hanging by the ankles. With the body hanging freely, normal gravitational pull is reversed thus causing a therapeutic effect on bone structure, spinal column, muscles, internal organs and body fluids.

U.S. Pat. No. 3, 685,511 (1972) to Alvarez describes an apparatus which stretches the backbone of a patient while simultaneously providing beneficial massage to the patient's body.

U.S. Pat. No. 3,081,085 (1963) to DeGirolamo similarly shows a health table intended to promote proper posture, accomplished through combined flexing and stretching of the back and spine of the patient while supported on the posture board.

U.S. Pat. No. 4,103,681 (1978) to Shanley similarly discloses a tilting traction apparatus where the patient, again lying on his back, is rotated about a pivot point to treat back injury or postural misalignment.

In a broader sense, the general principles of flexion, rotation and distraction of the spine are well known and have been effected in various strap and/or harness arrangements, alone or in combination with rotating-pivot type tables as described above. Examples thereof include U.S. Pat. No. 4,205,665 (1980) to Burton, and numerous products illustrated in the 1951 "Tables by Tower" catalog.

A tiltable table now offered to chiropractors is the so-called auto-track table sold by the Chattanooga corporation.

The related foreign references known to the inventor are French Pat. No. 1,291,572 (1962) to Cassin and Swedish Pat. No. 171,985 (1954) to Tyskland.

None of the above references define a table capable of pre-setting a patient's position prior to lift and of dynamically lifting the patient from the ground, selectively changing angles of flexion and extension of a patient's upper torso relative to his lower torso while effecting a change of the overall position of the patient relative to the gravity vector. The present invention particularly provides means for changing the degree of distraction of the spine. It will, therefore, be seen that the prior art does not address or otherwise consider many of the problems solved, and advantages achieved, by the Applicant's invention herein.

SUMMARY OF THE INVENTION

The invention relates to a rotatable treatment table for effecting extension and distraction of the spine of the patient. The inventive tiltable table includes a weighted platform adapted to rest upon a floor, the platform having a pivot means. Also provided are rigid, elongate support means having a lower end and upper end, said lower end secured to a fixed point of said platform. Further provided is extensible elongate elevation means having a lower and upper end, said lower end rotationally secured to said platform pivot means in which movement of said upper end relative to said lower end occurs at upper and lower ends. Also provided is a rigid rectangular support frame, having a head end and a foot end, the frame proportioned to extend beyond the length of the body of the patient, said support frame pivotally secured, proximally to its center of gravity, to the upper ends of said rigid and extensible elevation means.

Said pivotal securements of the frame to the upper ends of said elevation means define a vertical to horizontal selectable curved path of said frame relative to the weighted platform. Also provided is a center and lower back support assembly transversely mounted to said rectangular frame proximally to said upper ends of said elevation means in which the center of gravity of the patient is within said center and lower back assembly. This assembly more particularly comprises a plurality of pads having axes disposed transversely to said rigid raectangular frame and means for adjusting the location of the axes relative to each other and relative to said rigid rectangular frame such that a desired corrective curvature of the back can be imparted to the patient by the selective adjustment of said axes of said rollers.

The table also includes an upper back support transversely mounted to said rectangular frame headwardly of said center and lowerback support assembly. Also provided is a head support assembly transversely mounted to said frame headwardly of the said upper back assembly. Further provided is a leg support assembly transversely mounted to said rest platform legwardly of said center and lower back assembly. Each of said leg, upper back, and head support assemblies are provided with means for positional adjustment in a plane normal to the plane of said rigid frame to thereby permit imparting of a curvature to the upper or lower body relative to the center of gravity of the body of the patient.

The principal object of the invention is to provide a table which can effectuate flexion and extension of the spine, as may be required in the treatment of spinal disorders and/or maintenance of proper human posture, in such a manner that the relative positions of the patient's legs, lower back, head and shoulders can be varied.

Another object of the invention is to provide a treatment table which has a range of motion of zero to at least ninety degrees.

A further object is to provide a table that positions the patient in such a manner that the neck can, in concert with treatment of the spine, be more easily adjusted.

A still further object is to provide a treatment table which has a variety of adjustments so that patients of widely disparate age, height and weight can be accommodated.

A yet further object of the invention is to provide a table that is safe to use and simple to operate.

Other objects and advantages of the invention will become apparent from the detailed description of the invention, the drawings and the claims appended herewith.

BRIEF DESCRIPTION OF THE DRAWINGS

FIG. 3 is a schematic operational view of the roller pad assembly of the mid and lower back support assembly, taken during along 3—3 of FIG. 2.

FIGS. 4 and 5 are views of the leg support assembly. FIG. 4 is taken along Line 4—4 of FIG. 2.

FIGS. 6 and 7 are views of the locking means of the assembly of FIG. 3.

DETAILED DESCRIPTION OF THE INVENTION

Figure 1:
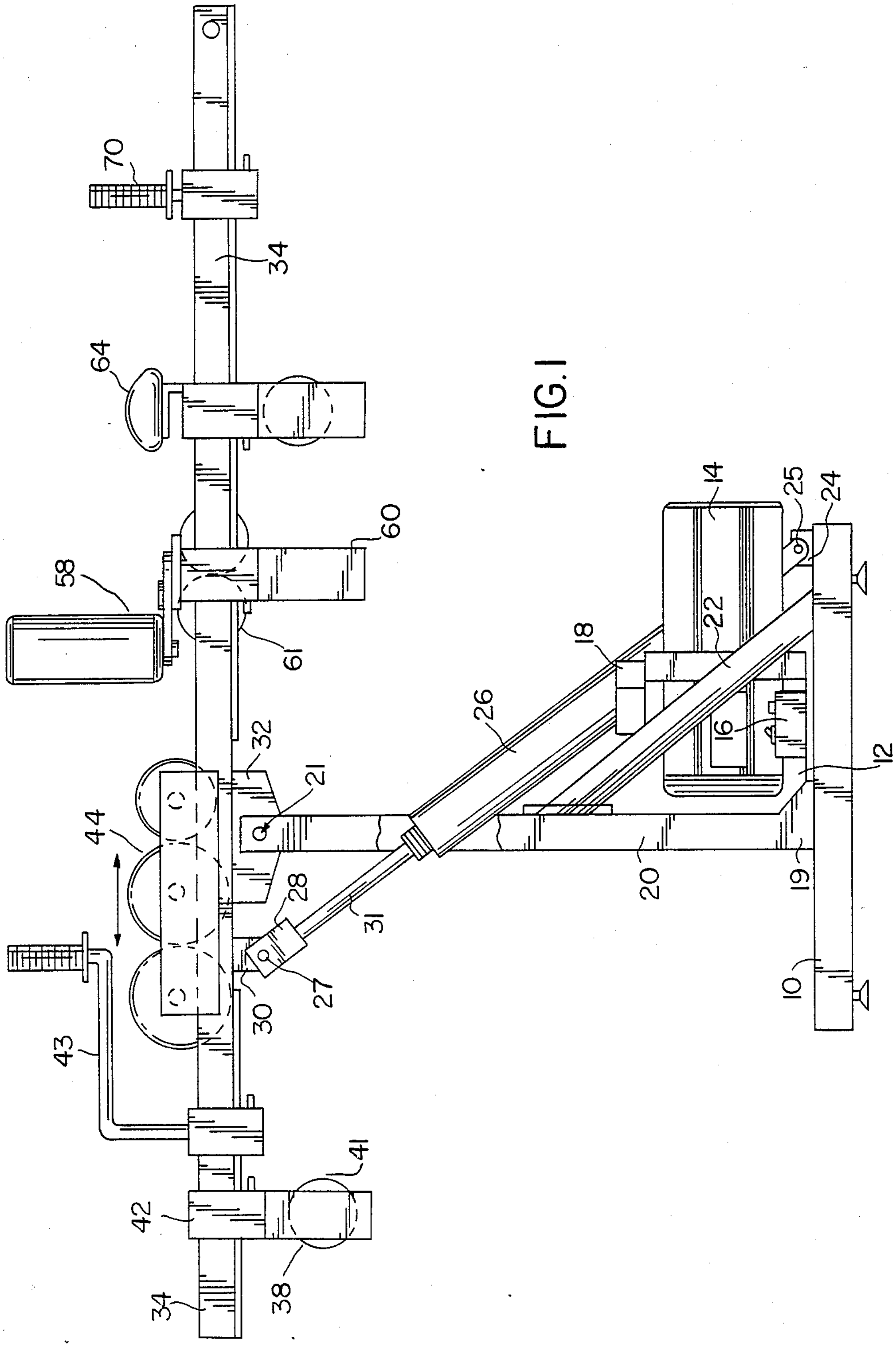
FIG. 1 is a front elevational schematic view of the inventive tiltable table.

With reference to FIG. 1, the inventive treatment table is shown in front schematic elevational view. Therein is shown weighted base 10 from which depends base plate 12; upon base plate 12 is positioned hydraulic means 14 together with its associated control means 16 and 18. Weighted base 10 is provided with a fixed point 19 and a pivot 25. To fixed point 19 is secured rigid elongate support means 20, which is connected to fixed point 19 at its lower end. Support means 20 is rigidly held by stiffener 22, preferably by bolts.

Connected to pivot point 25 is extensible elongate elevation means 26. As may be noted, extensible elevation means 26 includes a piston arm 31 which extends upwardly to upper end 28. The lower end of extensible elevation means 26 is secured to platform 10; its lower end connects to both pivot 25 and lower bracket 24 which connects to weighted base 10.

It is to be appreciated that the rotational movement around the upper end of rigid support means 20 about pivot 21 will define an axis of rotation. The rotation of the upper end of extensible elevational means 26 about pivot point 25 will define a segment of rotation which may, of course, vary with the degree of extension of piston arm 31.

Further shown in FIG. 1 is a rigid rectangular support 34 (see also FIG. 2) which, as well, consists of transverse support bars 35. The length of support frame 34 is proportioned to have a longitudinal length which will somewhat exceed the head-to-foot length of the body of the patient. Said rigid frame 34 is rotationally secured to the means 20 and 26 at pivot points 21 and 27 respectively. This more particularly is achieved through the use of integral bracket 30 which effects a rotational connection to the upper end 28 of piston 31 at pivot point 27, and through block support 32 which achieves the rotational connection of the upper end of rigid support means 20 at pivot point 21. Through this arrangement, rigid support frame 34 is capable of circumscribing, in a stable fashion, a plurality of positions from the vertical through the horizontal (See for example FIG. 10). The strength and stability afforded by the co-action of extensible elevation means 26 and rigid support means 20 indicates that the patient may be placed onto the table while standing, and totally secured within the treatment table while remaining standing. Thereafter, he may be gradually and dynamically lifted, with the assistance of the gravity vector on the patient's lower torso. In this fashion, if the table is elevated just slightly with reference to the vertical, the patient can be permitted to stretch, thereby providing the necessary traction, flexion and extension necessary to remove acute pain of the lower back and other conditions which occur in traumatic situations.

The above arrangement also minimizes the frictional resistance of the patient's lower torso (lumber spine, legs and pelvis) to efforts of traction by combining the use of gravity and the patient's own weight with the use of pads (below described) to allow the body to conform to said pads and to generally roll-over from the vertical to the horizontal position, or vice versa.

Also, as will be appreciated, the present table, as well as less elaborate equivalents thereof, may be employed in the self-administration of traction and in other exercises. Accordingly, the present invention may be understood and be useful in self-treatment as in treatment by a doctor of chiropractic.

The path of movement of rigid frame 34 relative to platform 10 is determined by both the length of elevation means 20 and 26 and by the separation of pivot points 21 and 27.

Figure 2:
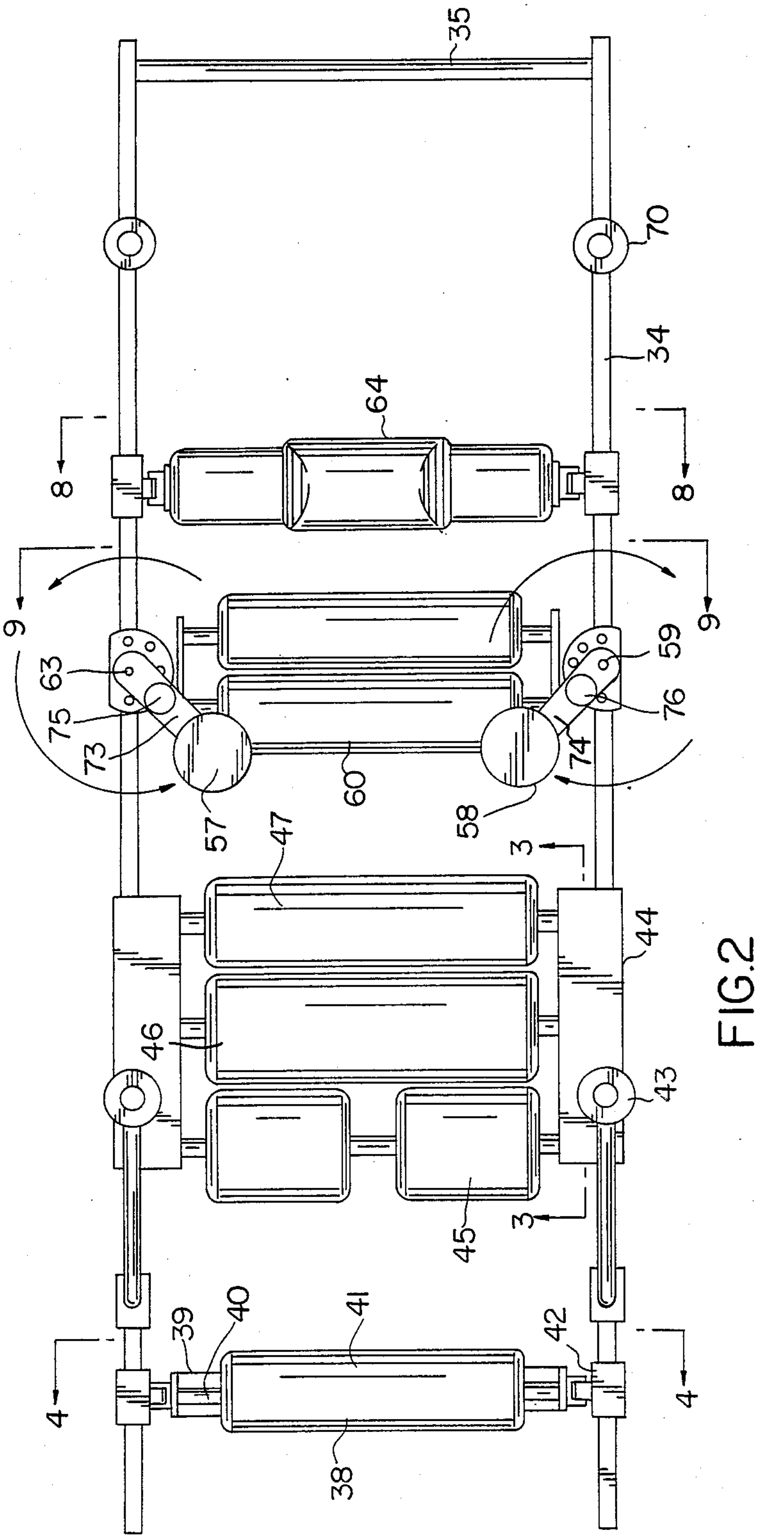
FIG. 2 is a top view thereof.

With further reference to FIGS. 1 and 2, there is seen a center and lower back support assembly 44 which is transversely mounted to frame elements 34 and 35 in a position which straddles said pivot points 21 and 27. In the embodiments shown in FIGS. 1 to 3, said assembly 44 is seen to consist of three pads, namely, pads 45, 46 and 47. A patient will, typically, be positioned upon said assembly 44 such that his center of gravity (usually corresponding to the lumbo-scacral region or area of the spine) will be disposed near or upon center pad 46. Said center and lower back assembly 44 comprises said pads 45, 46 and 47 and means for adjusting the axes of said pads relative both to each other and relative to rigid rectangular frame 34. Thereby, a desired corrective curvature of the back can be imparted to the patient by the selective adjustment of said axes of said pads of said center and lower back assembly 44.

In the embodiment of assembly 44 shown in FIG. 3, there may be seen pad axes 48, 49 and 50, respectively. It is seen that the right angle element 51 connects a third axis 50 with second axis 49 in a manner which is controlled by spring 54 which holds right angle element 51 to housing 53. Through this arrangement, axis 50 of third pad 47 may be rotated relative to axis 49 of second pad 46. Similarly, right angle element 52 rotationally secures first axis 48 to second axis 49 through a spring connection 55. Thereby, first pad 45 is capable of angular motion relative to axis 49 of second pad 46.

FIG. 6 is a lateral view of center and lower back support assembly 44, also shown in FIG. 1, having the cover plate removed, resting on a portion of support frame 34. Shown therein is the location of circular pads 45, 46, and 47, as well as the position of lock means 56 and housing 53.

With the reference to FIG. 7, as threaded knob 77 is turned clockwise into the threaded blocks of position and lock means 56, the blocks approach each other and create a frictional resistance against support frame 34. This allows center and lower back assembly 44 to either remain stationary or to adjust and vary its position along bar 34.

As is indicated in FIG. 1, pads 45, 46 and 47 may also be moved longitudinally by sliding the frame which connects said pads to horizontal frame 34. An example of the effects which may be achieved through the pad adjustment means shown in FIGS. 3, 5 and 7 is apparent by viewing of the schematic views of FIGS. 10 and 11. These views reflect but two of numerous possible curvatures which may be achieved through the adjustment of center and lower back assembly 44 using the pad adjustment system described and shown with reference to FIGS. 3, 6 and 7.

With further reference to FIGS. 1 and 2, there is shown upper back support assembly 60 which is transversely mounted upon said rectangular frame 34 and headwardly of said assembly 44. Assembly 60 in the preferred embodiment consists of two pads 61, as is shown in FIGS. 1, 2, 10, 11, and 12. Thereby, support is offered to the patient's upperback or chest depending upon whether the patient is resting against it in the supine or prone position. The pads are attached to frame 62 by shaft 72.

Figure 9:
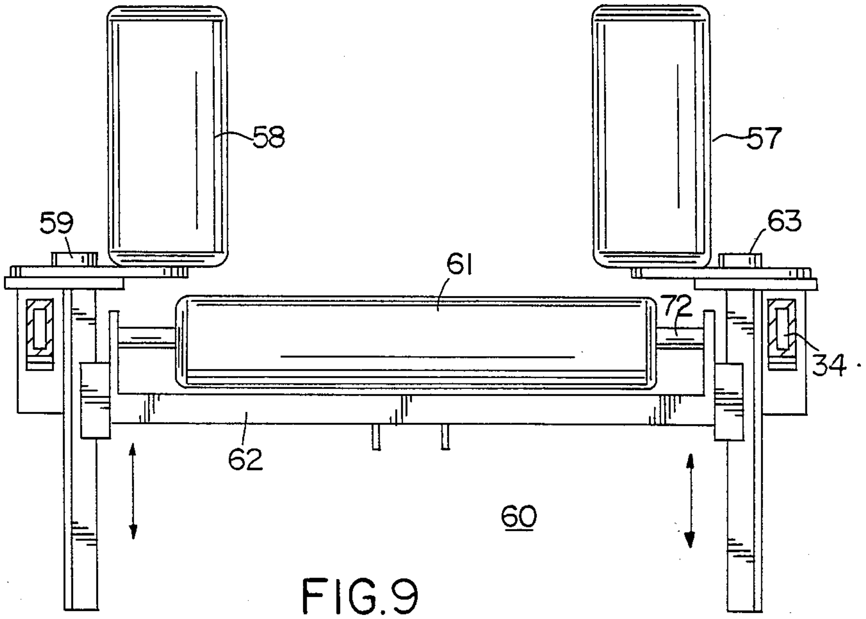
FIG. 9 is a detailed view of the upper back and arm support assemblies, taken along Line 9—9 of FIG. 2.

With reference to detail of FIG. 9, assembly 60 may be seen to be capable of positional adjustment in a plane normal to the plane of said rigid frame 34. Thereby, curvature of the upper body of the patient, headwardly of the center of gravity of patient's body may be thereby controlled.

Operating in association with said back support assembly 60 is an arm support assembly (see FIGS. 2 and 9). Therein it may be appreciated that the vertical padded elements 57 and 58 are pivoted about points 59 and 63 in a plane normal to the plane of rigid frame 34. Padded elements 57 and 58 are attached to arms 73 and 74 respectively, housing spring and polar interlock means 75 and 76 which consist of a small steel pin which is spring loaded. As arms 73 and 74 rotate around points 59 and 63, steel pins under spring tension are forced by the pressure of the springs into holes on support assembly 60.

The range of motion of pads 57 and 58 may be seen in FIG. 2 with reference to the circular arrows. The function of these arms supports are to support not only the arms of the patient but, as well, to generally confine the body of the patient with regard to possible undesired transverse movement. See FIGS. 10 and 11. Accordingly, arm support assembly 57 is of importance primarily because of its safety function. Secondarily, support assembly 57 may be employed with or without the use of hand grips 43 and 70 (later described) to easily lift the patient without the use of a time consuming thoracic harness which is commonly necessary for patients that are weak or elderly. It is it be appreciated that a wide strap VELCRO (a hook and loop) fastener may be applied under and across the patient's rib cage from one side of the lumbar support to the other. This employed in combination with support assembly 57.

Figure 8:
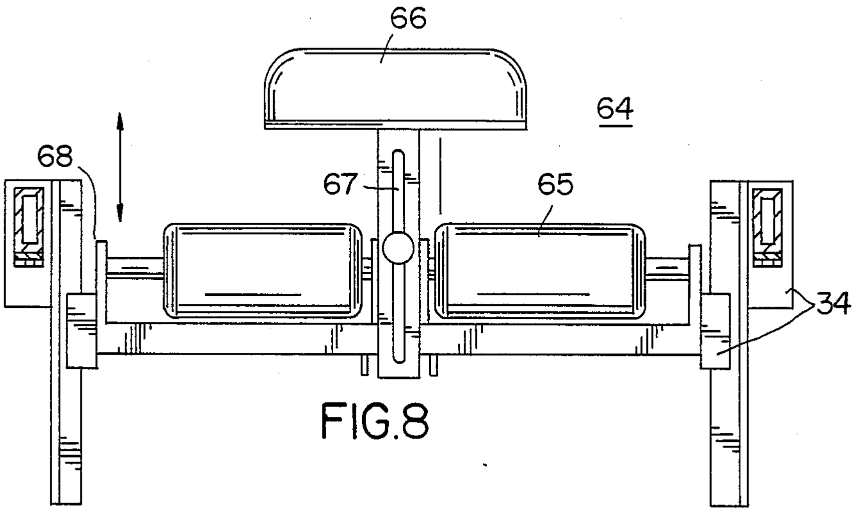
FIG. 8 is a detailed view of the head support assembly, taken along Line 8—8 of FIG. 2.

With reference to FIGS. 1, 2 and 8, may be seen head support assembly 64 which is transversely mounted to the rectangular frame 34 headwardly of the upper back support assembly 60. The head support assembly, as in the case of the upper back support assembly, is capable of positional adjustment in the plane normal to that of said frame 34. Thereby, curvature of the upper spine and the degree of extension and distraction applied thereto may be carefully controlled. Forearm supports pads 65 attach to head support assembly 64 and head and face pad 66 attaches to slide adjustment bar 67 for purposes of raising or lowering the head.

With further reference to FIGS. 1,2, 4 and 5, there is shown leg support assembly 38 transverse the plane of said rectangular frame 34 legwardly of said center and lower back assembly 44. This leg assembly comprises a round cushion 41 positionally adjustable in a plane normal to the plane of said rigid frames 34 and 35. Thereby the curvature of the lower back, legwardly of the center of gravity of the body, may be carefully controlled for purposes of selective lateral flexion, flexion extension and distraction of the lower spine. Leg support assembly 38 may, with reference to FIGS. 2,4 and 5, be seen to further include frame 39, shaft 40, round cushion 41, and vertical slide mechanism 42. Accordingly, leg support assembly is provided with an upward and/or downward positional adjustment capability in the plane normal to be plane of rigid frames 34 and 35, similar to that provided in association with upper back support 60 and head support assembly 64 (above described). It is to be appreciated that the roller of each of said assemblies are selectively removable.

The bars 78 and spring 79 of FIG. 4 comprise a locking mechanism used to raise, lower and to lock into position in a plane normal to the plane of said rigid frame 34.

Both right angles of bars 78 protruding down through the frame may be squeezed together causing a retracting of the distal ends of both bars from the holes found in both sides of each of the vertical slide mechanisms 42. The springs 79 function to keep the distal two ends of the pins extended into the holes 80 of vertical slide mechanism 42. This allows one to raise, lower and to make stationary the assembly of FIGS. 4 and 5.

Figure 10:
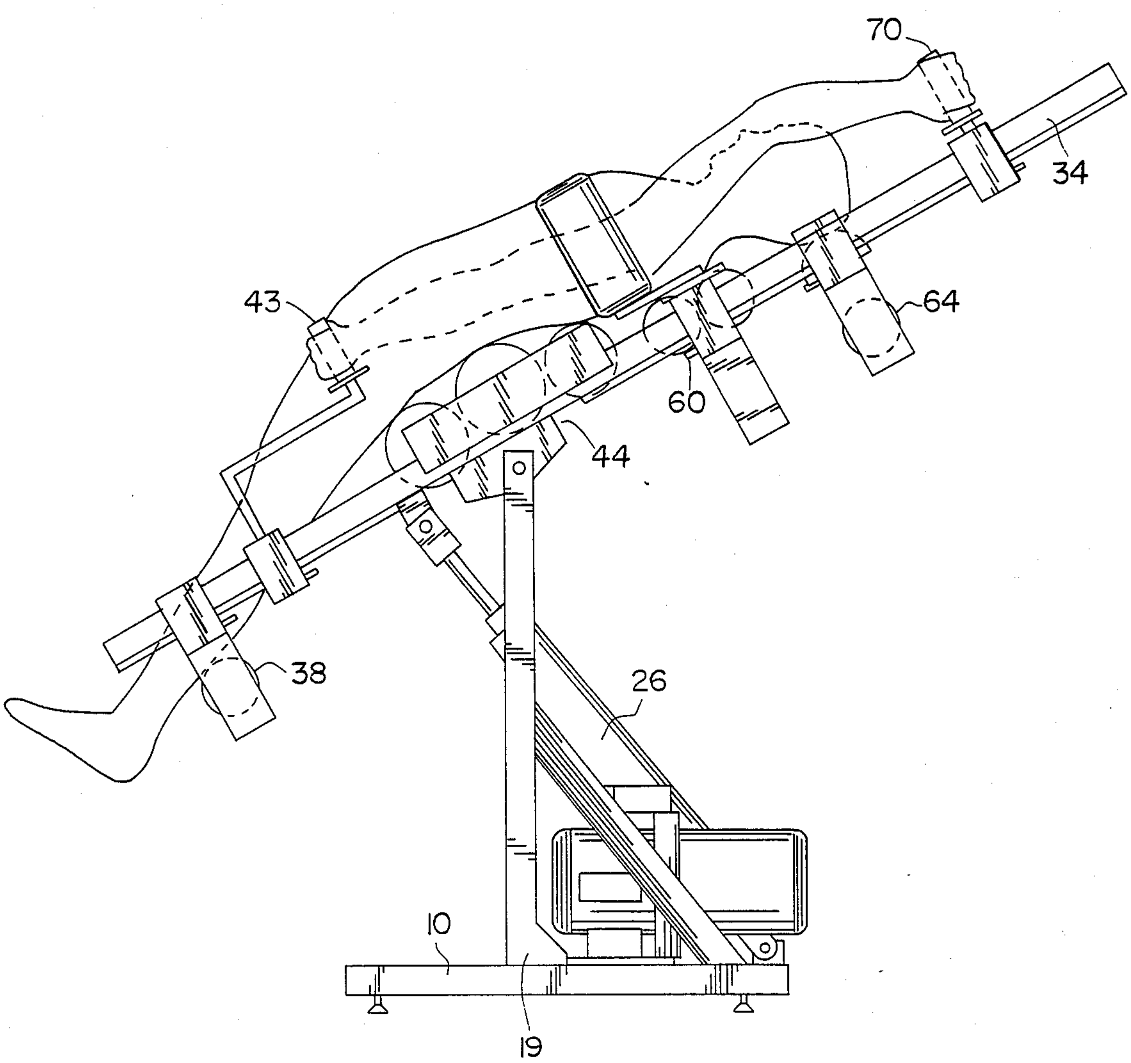
FIG. 10 is a first operational view of the invention.
Figure 11:
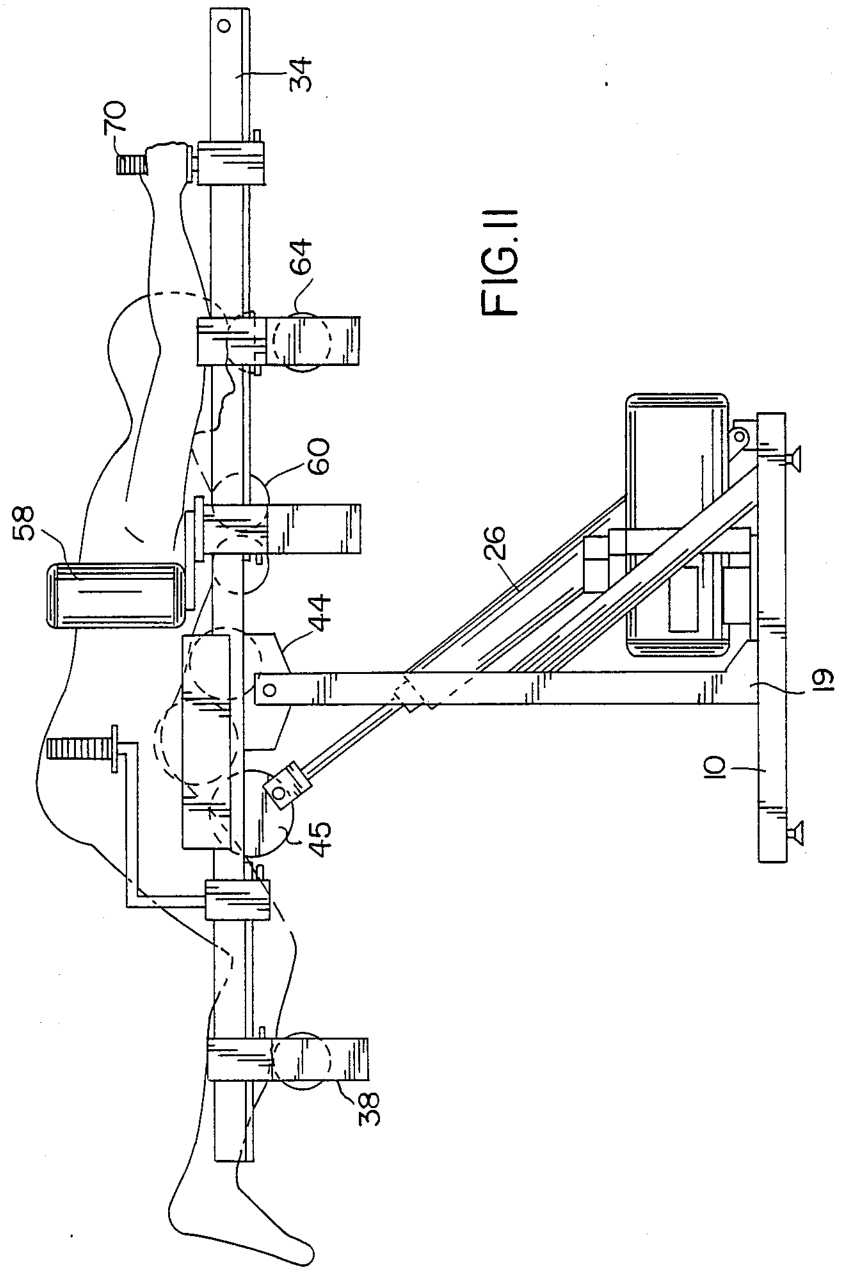
FIG. 11 is a second operational view thereof.

Through the use of the above-described tiltable treatment table, a variety of therapeutic effects upon the spine of the patient may be effected through the interaction of (1) the selective angular (vertical through horizontal) adjustment of said rigid frame relative to said weighted platform and (2) the change in the position relative to the plane of rigid support 34 of any combination of leg assembly 38, upper back assembly 57 and head support 64. The precise lower back curvature and gravity traction effect deemed to be appropriate by the physician may be achieved through the adjustment of the component pads of center and lower back assembly 44, as well as of the other support assemblies. Two of the many possible ways in which the present tiltable treatment table may be used are shown in FIGS. 10 and 11. In FIG. 10 the patient is shown in a supine position in which the pads of leg support 38 have been dropped relative to the plane of rigid frame 34. In this mode, extension or stretching is seen. Also, the manner in which the patient will grip lower gripping means 43 and upper gripping means 70 is also shown. The table in FIG. 10 is at an angle of about 60 degrees relative to platform 10. Cross-bar 35 may be employed as a hand support or as a strap support for a thoracic harness.

In FIG. 11, the patient is shown in a prone position. Here the table is approximately horizontal and, as well, the pads of mid and lower back assembly 44 have been oriented in a fashion selected by the doctor.

In the invention as above-described, it is to be appreciated that the number of pads may be varied, as may be their consistency and diameter. For example, cylindrical air bags or contoured cushions may, in certain patient situations, be preferable to the use of padded rollers. As above-noted, the underlying strength of the instant invention is that it permits the patient to remain in a desired position of extension, flexion and lateral flexion, while selectively variably rotating the platform which the patient is on to thereby selectively decrease or increase the tractional gravitational pull. This is achieved simply by altering the angle of the patient platform independently of the patient position.

The instant table permits various active exercises thereon by a patient in many positions. One of the benefits of this is the increase of passive, gravitational traction pull while imparting strength to the lower back, stomach and musculature of the leg. As above noted, the table may be employed by one having no diagnosable problem but who, simply, is interested in enhancing the health of his or her spine. It is also to be appreciated that a hospital bed may be designed employing the principles above set forth.

Finally, it is to be appreciated that frame 34 may be provided with a selective pivot means such that the headward half of frame 34 may be selectively tilted relative to the legward half thereof.

Figure 12:
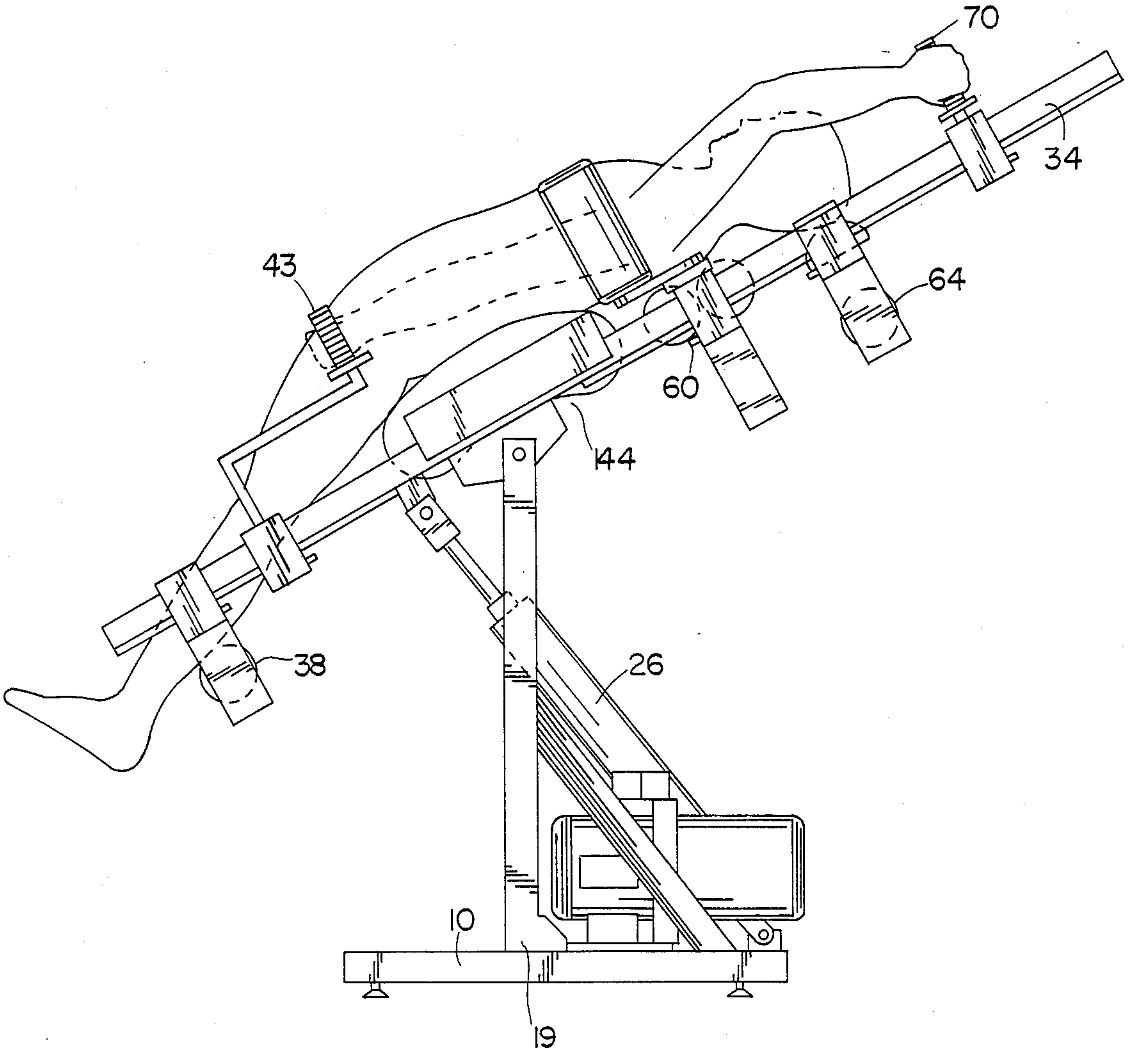
FIG. 12 is a side schematic view showing an alternative embodiment of the center and lower back support assembly.

With reference to FIG. 12, there is shown an alternative embodiment of the center and lower back support assembly. In this embodiment there is shown an assembly comprising an integral, contoured lumbar support assembly 144 transversely mounted to said rectangular frame proximally to said upper ends of said elevation means, in which the center of gravity of the patient is within the longitudinal dimension of said assembly, said lumbar support assembly further comprising means for adjusting the radius of contour wherein a desired correction of the curvature of the back of the patient may be imparted to him.

While there has been shown and described the preferred embodiment of the present invention, it will be understood that the invention may be embodied otherwise than as herein specifically illustrated or described and that within said embodiments certain charges in the detail and construction, and the form of arrangement of the parts may be made without departing from the underlying idea or principles of this invention within the scope of the appended claims.

Having thus described my invention what I claim as new, useful and non-obvious and, accordingly, secure by Letters Patent of the United States is:

1. A rotatable treatment table for effecting extension and distraction of the spine of a patient, the table comprising:

(a) a weighted platform, adapted to rest upon a floor, having a pivot means;

(b) a rigid elongate support means having a lower end and an upper end, said lower end secured to a fixed point on said platform;

(c) extensible elongate elevation means having a lower end and an upper end, said lower end rotationally secured to said pivot means of said weighted platform, in which reciprocal movement of said upper end of said extensible elevation means relative to said lower end may occur;

(d) a rigid rectangular support frame, having a head end and a foot end, said rigid support frame pivotally secured, proximally to its center of gravity, to the upper end of said rigid support means and, further, pivotally secured, footwardly of said center of gravity of said frame, to the upper end of said extensible elevation means, wherein said pivotal securement of said support frame defines a selectable curved path of said framr relative to said weighted platform;

(e) a center and lower back support assembly transversely mounted to said rectangular frame proximally to said upper end of said elevation means, in which the center of gravity of the patient is within the longitudinal dimension of said center and lower back assembly, said assembly further comprising a plurality of pads having axes disposed transversely to said rigid rectangular frame, said axes being positionally adjustable to positions below the plane of said rigid frame, wherein a desired correction of the curvature of the back of the patient may be imparted;

(f) a head support assembly transversely mounted to said rectangular frame headwardly of said back support assembly, and positionally adjustable in a plane normal to said rigid frame, said adjustability having a range extending above and below the plane of said rigid frame; and (g) patient gripping means for permitting the patient to be held on to the treatment table during a dynamic uplift thereof.

2. The treatment table recited in claim 1, further comprising:

a leg support assembly transversely mounted to said rectangular frame legwardly of said center and lower back assembly, the leg assembly comprising a cushion positionally adjustable in a plane normal to said rigid frame, said adjustability having a range extending below the plane of said rigid frame, in which the curvature of the lower body, legwardly of the center of gravity to the body may be thereby regulated, thereby a variety of therapeutic effects upon the spine of the patient may be affect through (1) dynamic lifting of the patient from the ground, (2) selective positional adjustment of said rigid frame relative to said weighted platform and (3) change in position of either or both of said back assemblies and said leg support assembly relative to the patient's center of gravity.

3. The treatment table recited in claim 1, in which said extensible elevation means further comprises a hydraulic cylinder for use in effecting the change in length of said elevational means and for providing support to the rigid frame both during static and dynamic conditions of the frame relative to the platform.

4. The treatment table recited in claim 1, in which said head support assembly further comprises a plurality of cushioned pads positionally adjustable at a plane normal to said rigid frame, whereby the curvature of the upper body, above the shoulders, may be thereby regulated.

5. The treatment table as recited in claim 1, further comprising: an upper back support assembly transversely mounted to said rectangular frame headwardly of said center and lower back support assembly, said assembly comprising a plurality of cushioned pads positionally adjustable in a plane normal to said rigid frame, in which the curvature of the upper body, headwardly of the center of gravity of the body may be thereby controlled.

6. The treatment table as recited in claim 5, further comprising: a leg support assembly transversely mounted to said rectangular frame legwardly of said center and lower back assembly, the leg assembly comprising a cushion positionally adjustable in a plane normal to said rigid frame, said adjustability having a range extending below the plane of said rigid frame, in which the curvature of the lower body, legwardly of the center of gravity to the body may be thereby regulated, to whereby a variety of therapeutic effects upon the spine of the patient may be affected through the (1) dynamic lifting of the patient from the ground, (2) the selective positional adjustment of said rigid frame relative to said weighted platform and (3) the change in position of either or both of said back assemblies and said leg support assembly relative to the patient's center of gravity.

7. The treatment table as recited in claim 6, in which said pads of said center and lower back support assembly comprise three pads having means for adjusting the polar position of the axes of the first and third pads relative to the axis of the second pad in which each axis of said first and third pads is capable of defining an arc of rotation relative to the axis of said second pad in which said arcs of rotation may pass both above and below said plane of said rigid frame.

8. The treatment table is recited in claim 6, in which said patient gripping means comprises:

an arm support assembly rotatably disposed on said rigid frame proximally to said upper back support assembly, said arm support assembly further comprising pads disposed normally into the plane of said rigid frame and rotationally moveable within an arc of rotation parallel to said rigis frame, said arm support assembly further including polar interlock means for yieldingly and rigidly fixing the polar position of said arm support assembly relative to the arms of the patient.

9. The treatment table as recited in claim 5, in which said patient gripping means comprises:

lower handle grip means positioned intermediately between said leg support, and center and lower back support assembly; and upper handle grip means positioned headwardly of said head support assembly, each of said gripping means comprising substantially linear elements directed substantially normally to the plane of said rigid frame.

10. The treatment table as recited in claim 9, in which said pads of said center and lower back support assembly comprise three pads having means for adjusting the polar position of the axis of the first and third pads relative to the axis of the second pad, in which each axis of said first and third pads is capable of defining an arc of rotation relative to the axis of said second pad, in which said arc may pass below said plane of said rigid frame.

11. The treatment table is recited in claim 9, in which patient gripping means comprises:

an arm support assembly rotatably disposed on said rigid frame proximally to said upper back support assembly, said arm support assembly further comprising pads disposed normally into the plane of said rigid frame and rotatably moveable within an arc of rotation parallel to said rigid frame, said arm support assembly further including polar interlock means for yieldingly rigidly fixing the polar position of said arm support assembly relative to the arms of the patient.

12. The treatment table is recited in claim 5, in which said patient gripping means comprises:

a rotatable arm support assembly rotatably disposed on said rigid frame proximally to said upper back support assembly, said arm support assembly further comprising pads disposed normally to plane of said rigid frame and rotatably moveable within an arc of rotation relative to said rigid frame, said arm support assembly further including polar interlock means for yieldingly and rigidly fixing the polar position of said arm support assembly relative to the arms of the patient to thereby assist in the holding of a patient safely on to the treatment table during its use.

13. The treatment table is recited in claim 12, in which said pads of said center and lower back support assembly comprised three pads having means for adjusting the polar position of the axis of the first and third pads relative to the axis of the second pad, in which each axis of said first and third pads is capable of defining an arc of rotation relative to the axis of said second pad, in which said arc may pass below said plane of said rigid frame.

14. A rotatable treatment table for effecting extension and extraction of the spine of the patient, the table comprising:

(a) a weighted platform adapted to rest upon a floor, having pivot means;

(b) rigid elongate support means having a lower end and an upper end, said lower end secured to a fixed point on said platform;

(c) extensible elongate elevation means having a lower end and an upper end, said lower end rotationally secured to said pivot means of said weighted plaform, in which a reciprocal movement of said upper end of said extensible elevation means relative to said lower end may occur, (d) a rigid rectangular support frame, having a head end and a foot end, said rigid support frame pivotally secured, proximally at center of gravity, to the upper end of said rigid support means and, further, pivotally secured, footwardly of said center of gravity to said frame, to the upper end of said extensible elevation means, wherein said pivotal securement of said support frame define a selectable path of said frame relative to said weighted platform;

(e) an integral, contoured lumbar support assembly, transversely mounted to said rectangular frame proximally to said upper ends of said elevation means, in which the center of gravity of the patient is within the longitudinal dimension of said assembly, the contour of said lumbar support assembly including curvatures capable of extending below the plane of said rigid frame;

(f) a head support assembly transversely mounted to said rectangular frame headwardly of said back support assembly and discretely adjustable in a plane normal to the plane of said rigid frame, said adjustability having a range extending above and below the plane of said rigid frame; and (g) patient gripping means for permitting the patient to be held on to the treatment table during a dynamic uplift thereof.

15. The treatment table as recited in claim 14, further comprising:

a leg support assembly transversely mounted to said rectangular frame legwardly of said lumbar assembly, the leg assembly comprising a cushion positionally adjustable in a plane normal to said rigid frame, said adjustability having a range extending below the plane of said frame, in which the curvature of the lower body, legwardly of the center of gravity to the body may be thereby regulated, whereby a variety of therapeutic effects upon the spine of the patient may be affected through the interaction of (1) the selective angular adjustment of said rigid frame relative to said weighted platform and (2) the change in angular position of either or both said lumbar assembly and said leg support assembly relative to the patient's center of gravity.

16. The treatment as recited in claim 14, patient gripping means comprising:

lower handle grip means positioned intermediately between said leg support and said lumbar support assembly; and upper handle grip means positioned headwardly of said head support assembly, said upper and lower handle grip means comprising of substantially linear elements directed substantially normally to the plane of said rigid frame.

17. The treatment table as recited in claim 16, patient gripping means further comprising:

a rotatable arm support assembly rotatably disposed on said rigid frame proximally to said upper back support assembly, said arm support assembly further comprising pads disposed normally to a plane of said rigid frame rotatably moveable within an arc of rotation relative to said rigid frame, said arm support assembly further including polar interlock means for fixing the position of said arm support assembly relative to the arms of the patient thereby assist in the lifting and holding of a patient safely onto the treatment table during its use.

18. The treatment table as recited in claim 14, further comprising: an upper back support assembly transversely mounted to said rectangular frame headwardly of said lumbar support assembly, said assembly comprising a plurality of cushion pads positioned adjustably in a plane normal to said rigid frame, said adjustability having a range extending below the plane of said rigid frame in which the curvature of the upper body, headwardly of the center of gravity of the body may be thereby controlled.

19. The treatment table is recited in claim 18 patient gripping means comprising:

an arm support assembly rotatably disposed on said rigid frame proximally to said upper back support assembly, said arm support assembly further comprising pads disposed normally to the plane of said rigid frame and rotationally moveable within an arc of rotation parallel to said rigid frame, said arm support assembly further including polar interlock means for fixing the position of said arms support assembly relative to the arms of the patient.

20. The treatment table as recited in claim 18, further comprising:

a leg support assembly transversely mounted to said rectangular frame legwardly of said lumbar assembly, the leg assembly comprising a cushion positionally adjustable in a plane normal to said rigid frame, said adjustablity having a range extending below the plane of said rigid frame, in which the curvature of lower body, legwardly of the center of gravity to the body may be thereby regulated, whereby therapeutic effects upon the spine of the patient may be affected through (1) a dynamic lifting of the patient from the ground, (2) the selective adjustment of said rigid frame relative to said rated platform and (3) change of position in either or both said lumbar assembly and said leg support assembly relative to the patient's center of gravity.

21. The treatment table recited in claim 20, in which said extensible elevation means further comprises a hydraulic cylinder for use in effecting change in length of said elevational means and for providing support to the rigid frame both during static and dynamic conditions of the frame relative the platform.

22. The treatment table recited and claim 20 in which said head support assembly further comprises a plurality of cushioned pads positionally adjustable at a plane normal to said rigid frame, whereby the curvature of the upperbody, above the shoulders, may be thereby regulated.

23. The treatment table is recited in claim 20 patient gripping means comprising: a rotatable arm support assembly rotatably disposed on said rigid frame proximally to said upper back support assembly, said upper support assembly further comprising pads disposed normally to the plane of said rigid frame and rotationally moveable within an arc of rotation parallel to said rigid frame, said arm support assembly further including polar interlock means for fixing the position of said arms support assembly relative to the arms of the patient.

* * * * *